United States Patent
Stigall et al.

(10) Patent No.: US 10,226,203 B2
(45) Date of Patent: Mar. 12, 2019

(54) DEVICE FOR ANATOMICAL LESION LENGTH ESTIMATION

(71) Applicant: Volcano Corporation, San Diego, CA (US)

(72) Inventors: Jeremy Stigall, Carlsbad, CA (US); Chris LeBlanc, San Diego, CA (US); Kazuo Sasamine, Lemon Grove, CA (US)

(73) Assignee: VOLCANO CORPORATION, San Diego, CA (US)

( * ) Notice: Subject to any disclaimer, the term of this patent is extended or adjusted under 35 U.S.C. 154(b) by 647 days.

(21) Appl. No.: 13/974,124

(22) Filed: Aug. 23, 2013

(65) Prior Publication Data

US 2014/0058251 A1    Feb. 27, 2014

Related U.S. Application Data

(60) Provisional application No. 61/692,612, filed on Aug. 23, 2012.

(51) Int. Cl.
*A61B 5/107* (2006.01)
*A61M 25/06* (2006.01)
(Continued)

(52) U.S. Cl.
CPC .............. *A61B 5/1076* (2013.01); *A61B 1/05* (2013.01); *A61B 5/6852* (2013.01); *A61B 6/12* (2013.01); *A61M 25/0662* (2013.01); *A61B 6/508* (2013.01); *A61B 2090/3937* (2016.02); *A61B 2090/3941* (2016.02);
(Continued)

(58) Field of Classification Search
CPC .............. A61B 1/05; A61B 2090/3937; A61B 2090/3941; A61B 2090/3966; A61B 5/1076; A61B 5/6852; A61B 6/12; A61B 6/508; A61M 2025/0004; A61M 2025/0008; A61M 2025/0059; A61M 25/0012; A61M 25/005; A61M 25/0108; A61M 25/0662
See application file for complete search history.

(56) References Cited

U.S. PATENT DOCUMENTS 5,174,302 A * 12/1992 Palmer .................. A61M 25/09
                                                                             600/434
5,851,210 A    12/1998 Torossian
(Continued)

FOREIGN PATENT DOCUMENTS

EP           597506 B1     12/1998
JP          2005-278905     10/2005
(Continued)

OTHER PUBLICATIONS

International Search Report and Written Opinion received in Patent Cooperation Treaty Application No. PCT/US2013/056320, dated Nov. 14, 2013, 17 pages.
(Continued)

*Primary Examiner* — Ruth S Smith

(57) ABSTRACT

An intravascular measurement system is provided. The system includes a catheter having a plurality of visible markers on a proximal portion that are proportional to a plurality of radiopaque markers on a distal portion. In at least one aspect, the system includes an imaging device adjacent the distal end.

20 Claims, 9 Drawing Sheets

(51) Int. Cl.
*A61B 1/05* (2006.01)
*A61B 6/12* (2006.01)
*A61B 5/00* (2006.01)
*A61M 25/01* (2006.01)
*A61M 25/00* (2006.01)
*A61B 6/00* (2006.01)
*A61B 90/00* (2016.01)

(52) U.S. Cl.
CPC .... *A61B 2090/3966* (2016.02); *A61M 25/005* (2013.01); *A61M 25/0012* (2013.01); *A61M 25/0108* (2013.01); *A61M 2025/0004* (2013.01); *A61M 2025/0008* (2013.01); *A61M 2025/0059* (2013.01)

(56) References Cited

U.S. PATENT DOCUMENTS

| | | | | |
|---|---|---|---|---|
| 2003/0195546 | A1* | 10/2003 | Solar | A61M 25/01 606/192 |
| 2004/0167496 | A1* | 8/2004 | Poole | A61L 29/18 604/529 |
| 2004/0267195 | A1 | 12/2004 | Currlin | |
| 2007/0250000 | A1* | 10/2007 | Magnin | A61B 8/12 604/103.04 |
| 2007/0265564 | A1* | 11/2007 | Daly | A61M 25/0108 604/103.1 |
| 2008/0108974 | A1 | 5/2008 | Roth | |

FOREIGN PATENT DOCUMENTS

| | | |
|---|---|---|
| JP | 2007-236472 A | 9/2007 |
| WO | WO 99/35979 A1 | 7/1999 |
| WO | WO 2006/118737 A1 | 11/2006 |
| WO | WO 2008/134382 A1 | 11/2008 |

OTHER PUBLICATIONS

The Hague/European Patent Office, "Supplementary European Search Report," for European Application No. 13830754.1, dated Mar. 23, 2016, 7 pages.

* cited by examiner

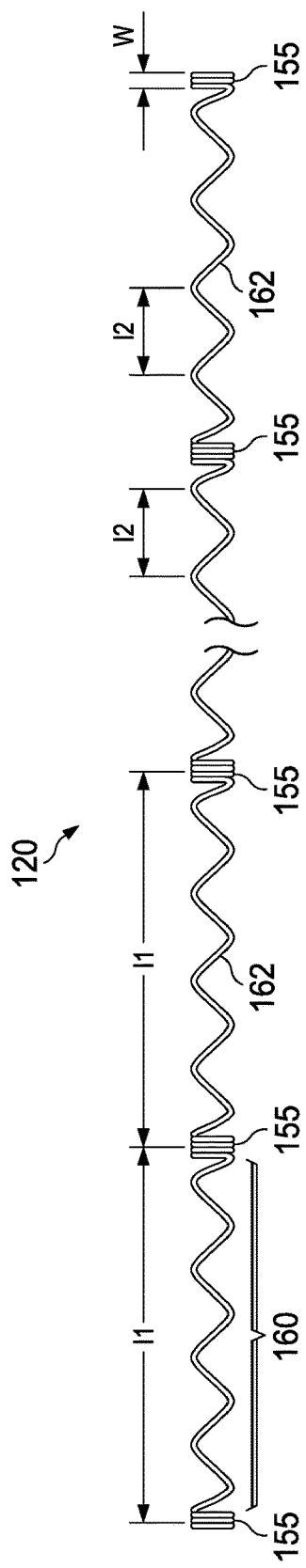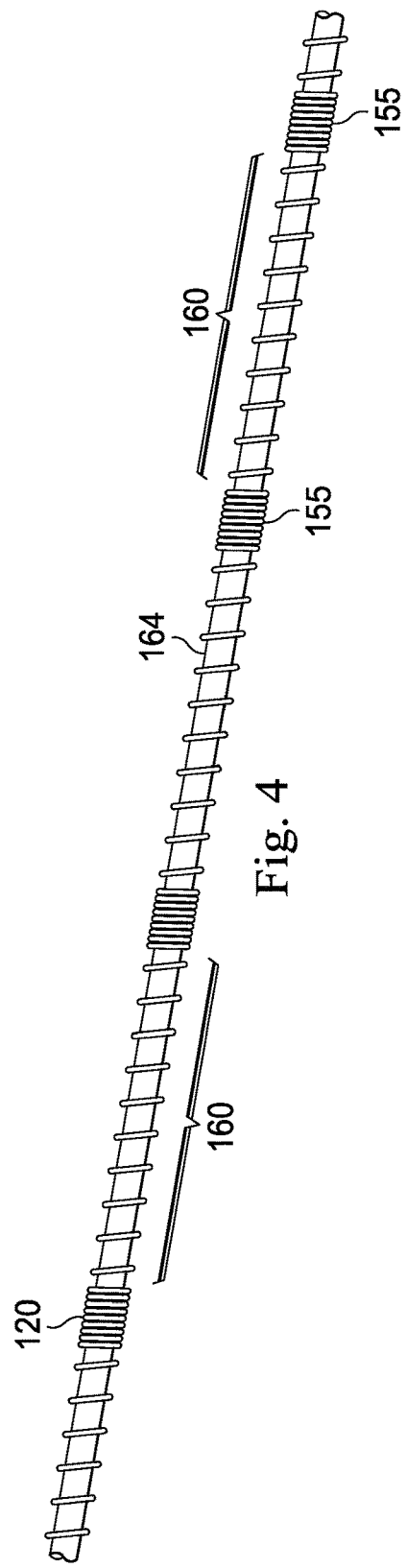

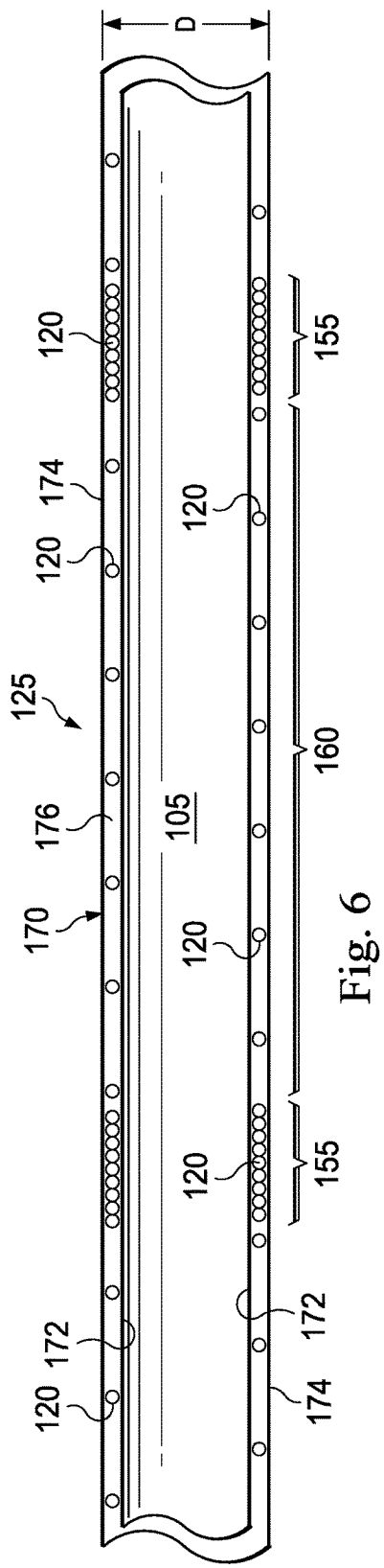
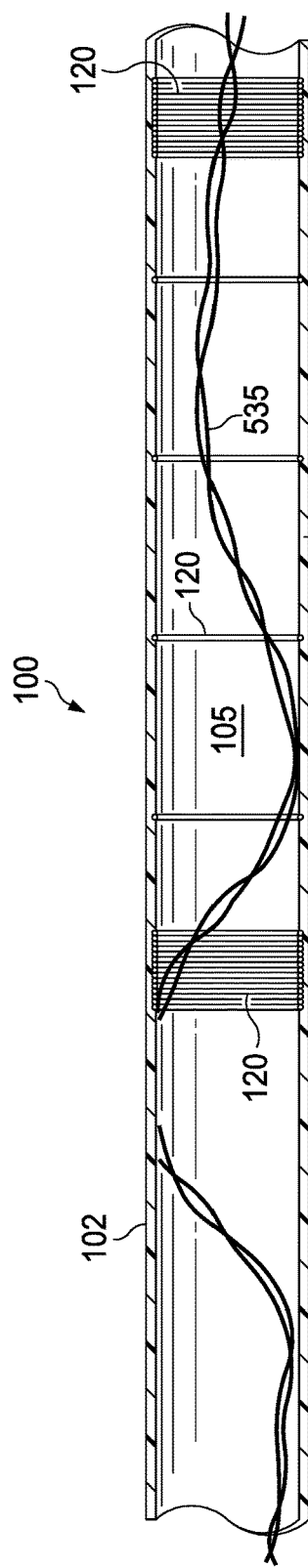

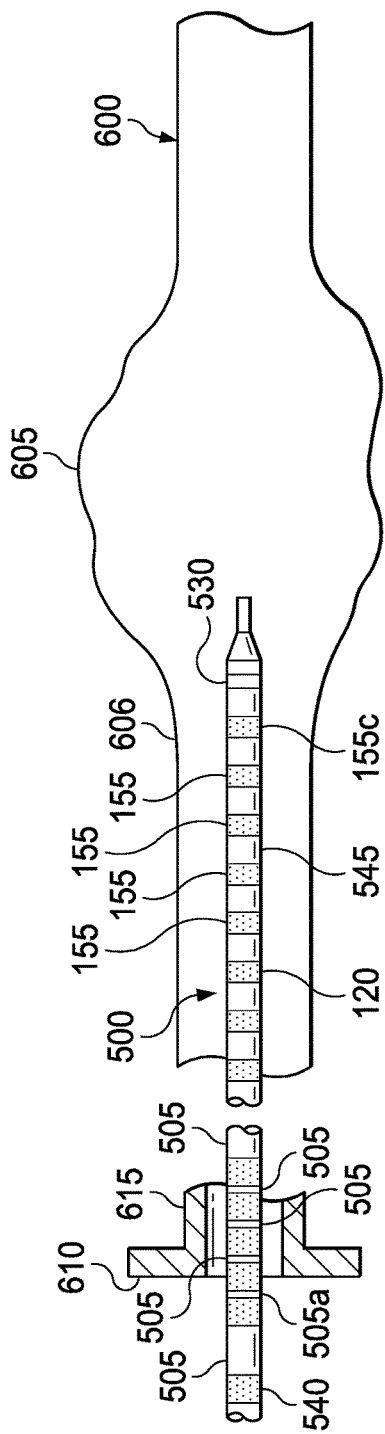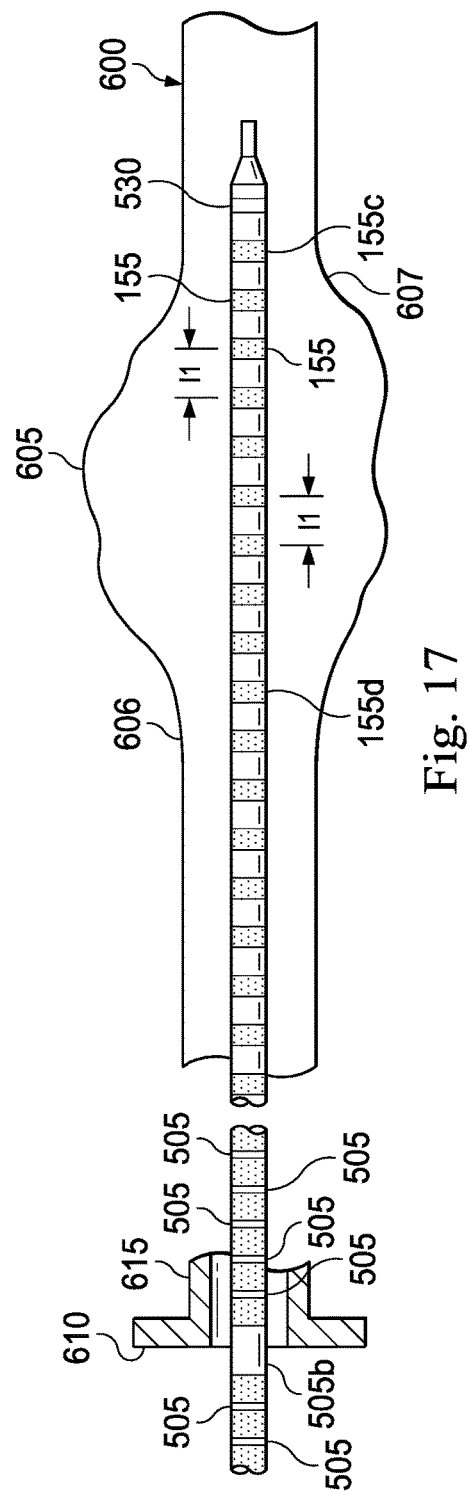

DEVICE FOR ANATOMICAL LESION LENGTH ESTIMATION

CROSS-REFERENCE TO RELATED APPLICATIONS

The present application claims priority to and the benefit of U.S. Provisional Patent Application No. 61/692,612, filed Aug. 23, 2012, which is hereby incorporated by reference in its entirety.

BACKGROUND

Catheters have widespread clinical use in both diagnostic and therapeutic procedures. For example, catheters are used diagnostically to inject contrast media, measure internal body dimensions, retrieve biopsy samples, and visually inspect internal body sites. Catheters are used therapeutically to deliver drugs, deliver implants, drain fluids, retrieve foreign and/or undesirable materials, deliver ultrasound, deliver laser light, provide access for minimally invasive surgical instruments, and dilate narrowed body passages (e.g., vessels).

In several of these procedures, it is advantageous to be able to visualize the progress of the catheter towards the target location within a patient's body. Introducing catheters into the body often requires fluoroscopic visualization to aid the treating healthcare provider in guiding the catheter to the target site. Catheters are commonly formed of a non-radiopaque polymeric material. Therefore, radiopaque markers may be added to the catheter to enable the catheter to be visualized during x-ray and fluoroscopic procedures. For example, in intravascular catheter procedures, health care providers may guide the catheter to a target location by using fluoroscopy to track the position of radiopaque markers on the catheter.

Commonly, these radiopaque markers are circumferential metallic bands affixed to the exterior surface of the catheter. Although these marker bands allow the catheter to be visualized by fluoroscopy, they can present certain problems. In particular, metallic marker bands require fixation (e.g., by crimping, swaging, or adhesive) to the underlying catheter to avoid slippage as the catheter is moved through the body. The bands may protrude from the tubular surface of the catheter and increase the catheter profile, which creates frictional resistance to the translational movement of the catheter through body passages, and potentially damages tissues contacting the moving catheter. In some instances, where a marker band has been swaged onto the outer surface of a catheter and the inner diameter of a marker band is greater than the outer diameter of the catheter, buckling may occur, causing the marker band to crack and the catheter surface to tear. Further, the placement of band markers on the outer catheter surface presents problems with inadvertent disassociation of the markers from the catheter wall, with attendant loss of positional and measurement accuracy. In addition, such marker bands are constructed from expensive and heavy radiopaque metals such as gold, platinum, tantalum, and alloys of these dense materials. The use of these heavy materials typically results in inflexible and rigid marker bands that can impair the trackability of the catheter by increasing the stiffness of the catheter, thereby compromising the flexibility and maneuverability of the catheter.

The devices, systems, and methods disclosed herein overcome one or more of the deficiencies of the prior art.

SUMMARY

In one aspect, the present disclosure provides a device for characterizing a structure within a body of a patient. In some embodiments, the device comprises a flexible elongate member and a plurality of visible markers. In some embodiments, the flexible elongate member comprises an inner tubular member disposed coaxially within an outer tubular member, with the inner tubular member defining a central lumen and the outer tubular member defining an annular lumen between the inner tubular member and the outer tubular member. In some embodiments, the plurality of visible markers is disposed on the inner tubular member.

In another aspect, the present disclosure provides a device for characterizing a structure within a body of a patient, the device comprising a flexible elongate member, a plurality of visible markers, and a radiopaque coil. In some embodiments, the flexible elongate member comprises an inner tubular member disposed coaxially within an outer tubular member, with the inner tubular member defining a central lumen and the outer tubular member defining an annular lumen between the inner tubular member and the outer tubular member. In some embodiments, the plurality of visible markers is disposed on the inner tubular member. In some embodiments, the radiopaque coil is disposed within the annular lumen. In some embodiments, the radiopaque coil comprises an alternating series of tightly wound sections and loosely wound sections.

In another aspect, the present disclosure provides an imaging system for characterizing and measuring a structure within a body of a patient. In some embodiments, the imaging system comprises a hollow, flexible elongate member and an imaging device coupled to the elongate member. In some embodiments, the elongate member comprises a proximal portion, a distal portion, and a uniform diameter. In some embodiments, the imaging system further comprises a plurality of visible markers on the proximal portion of the elongate member. In some embodiments, the imaging system further comprises a flexible radiopaque coil wound about the distal portion of the elongate member, the radiopaque coil including a plurality of tightly wound sections separated by loosely wound sections.

In another aspect, the present disclosure provides a method of characterizing a structure within a body of a patient. In some embodiments, the method comprises inserting an elongate member past an external reference point into the body, the elongate member including a plurality of inked markers separated by first intervals of constant length at a proximal portion of the elongate member and a radiopaque marker coil positioned at a distal portion of the elongate member, wherein the radiopaque marker coil has a plurality of radiopaque tightly wound sections separated by second intervals of constant length; positioning the radiopaque marker coil of the elongate member adjacent a first point of interest on the structure; observing a first radiopaque tightly wound section at the first point of interest of the structure; observing a first inked marker at the reference point; advancing the distal portion of the elongate member through the structure such that first radiopaque tightly wound section is at a second point of interest of the structure; observing a second radiopaque tightly wound section at the first point of interest of the structure; and observing a second inked marker at the reference point. In some embodiments, the method further comprises counting the number of second intervals separating the first radiopaque tightly wound section and the second radiopaque tightly wound section; calculating the linear distance between the first point of interest and the second point of interest of the structure by converting the number of intervals separating the first radiopaque tightly wound section and the second radiopaque tightly wound section into a linear measurement; counting the number of first intervals separating the first inked marker and the second inked marker; and confirming the linear distance between the first point of interest and the second point of interest of the structure by converting the number of intervals separating the first inked marker and the second inked marker into a linear measurement.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to those elements when referred to by the same reference number in another location unless specifically stated otherwise.

The figures referenced below are drawn for ease of explanation of the basic teachings of the present disclosure only; the extensions of the figures with respect to number, position, relationship, and dimensions of the parts to form the following embodiments will be explained or will be within the skill of the art after the following description has been read and understood. Further, the exact dimensions and dimensional proportions to conform to specific force, weight, strength, and similar requirements will likewise be within the skill of the art after the following description has been read and understood.

The following is a brief description of each figure used to describe the present invention, and thus, is being presented for illustrative purposes only and should not be limitative of the scope of the present invention.

Figure 1:
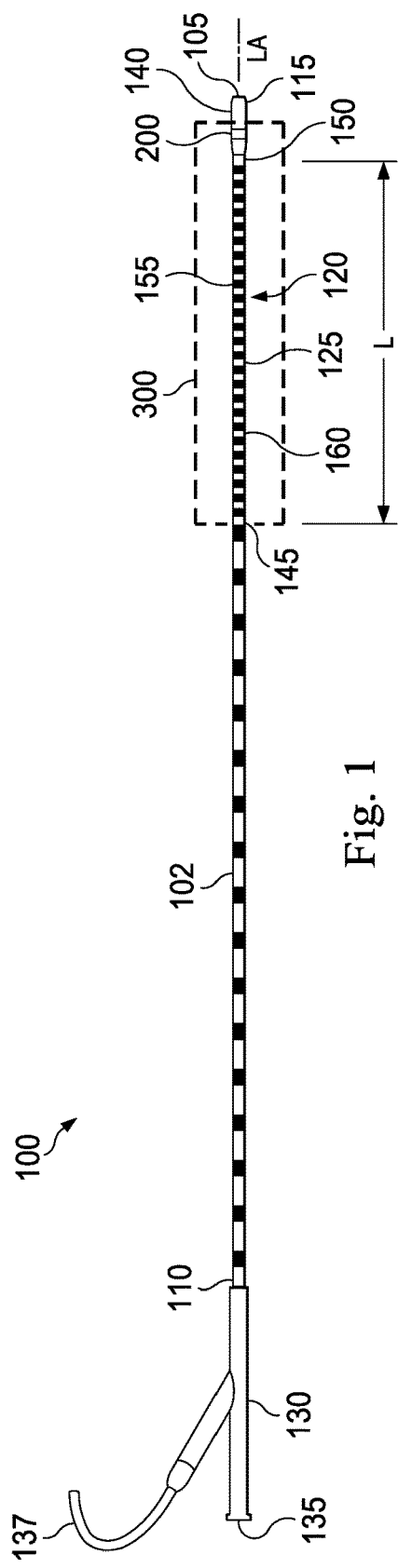

FIG. 1 is a diagrammatic illustration of an exemplary catheter according to one embodiment of the present disclosure.

Figure 2:
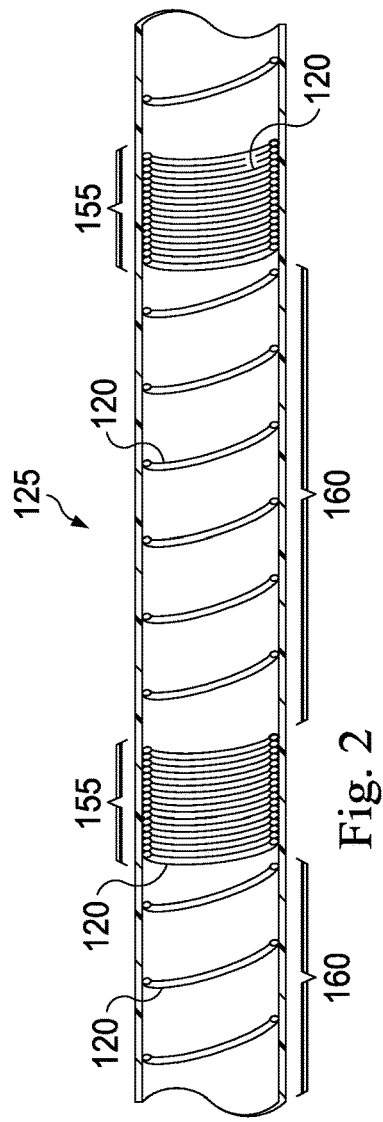

FIG. 2 is an illustration of a side view of a distal portion of the exemplary catheter shown in FIG. 1, including an exemplary marker coil according to one embodiment of the present disclosure.

FIG. 3 is a schematic illustration of the exemplary marker coil shown in FIG. 2.

FIG. 4 is an illustration of a perspective view of a portion of an exemplary marker coil according to one embodiment of the present disclosure.

FIGS. 5a-5d illustrate an exemplary method of manufacturing a marker coil on a mandrel according to one embodiment of the present disclosure.

FIG. 6 is an illustration of a cross-sectional view of a distal portion of the exemplary catheter shown in FIG. 1, including a portion of the exemplary marker coil shown in FIGS. 1 and 2.

FIG. 7 is a schematic illustration of an exemplary marker coil within an exemplary catheter according to one embodiment of the present disclosure.

Figure 8:
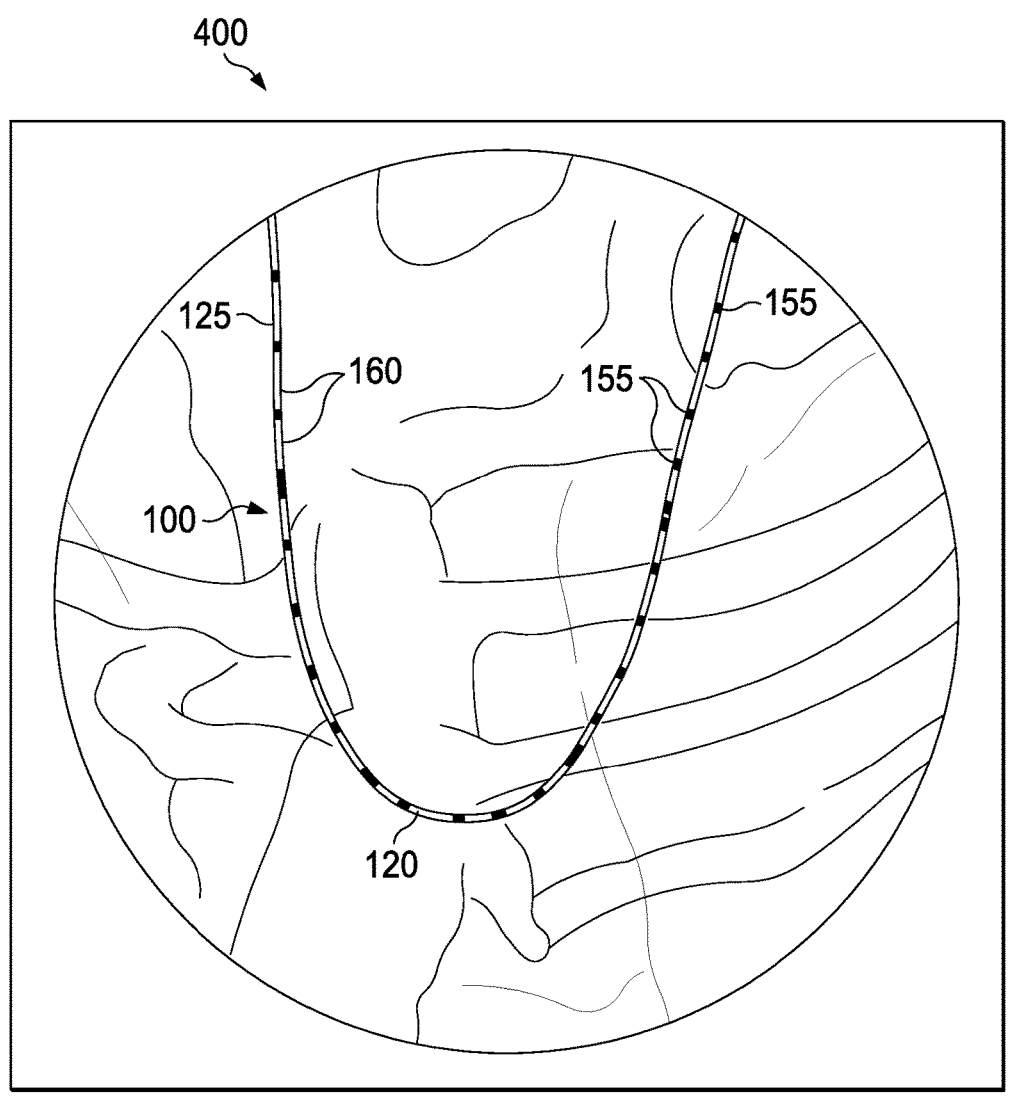

FIG. 8 is an exemplary static fluoroscopy image showing an exemplary marker coil within an exemplary catheter according to one embodiment of the present disclosure.

Figure 9:
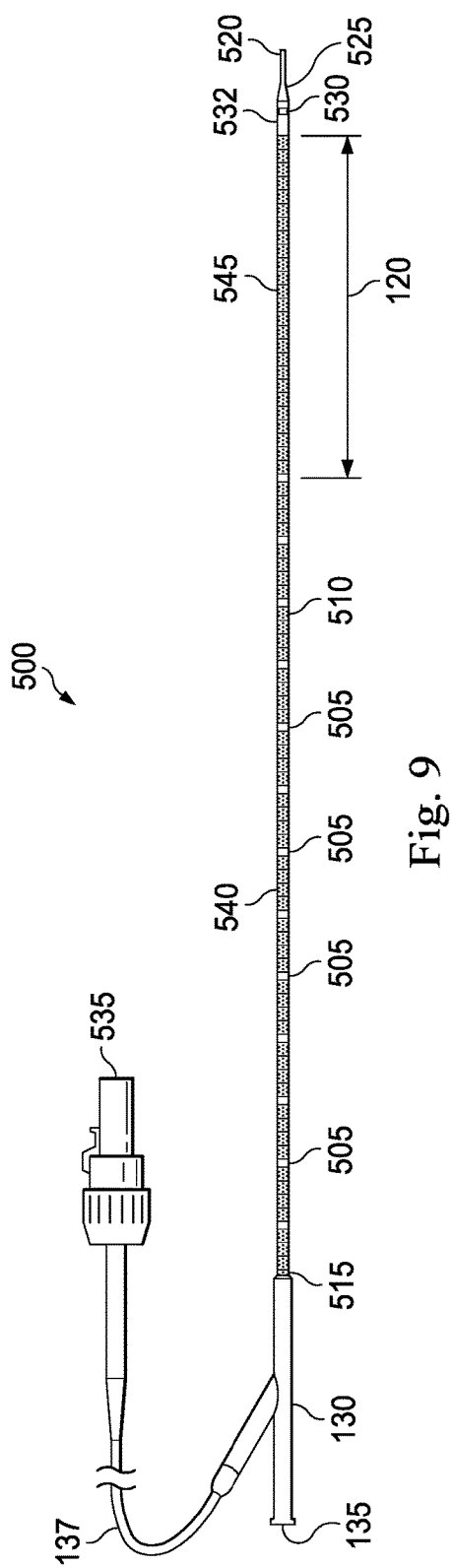

FIG. 9 is a diagrammatic illustration of an exemplary imaging catheter according to one embodiment of the present disclosure.

Figure 10:
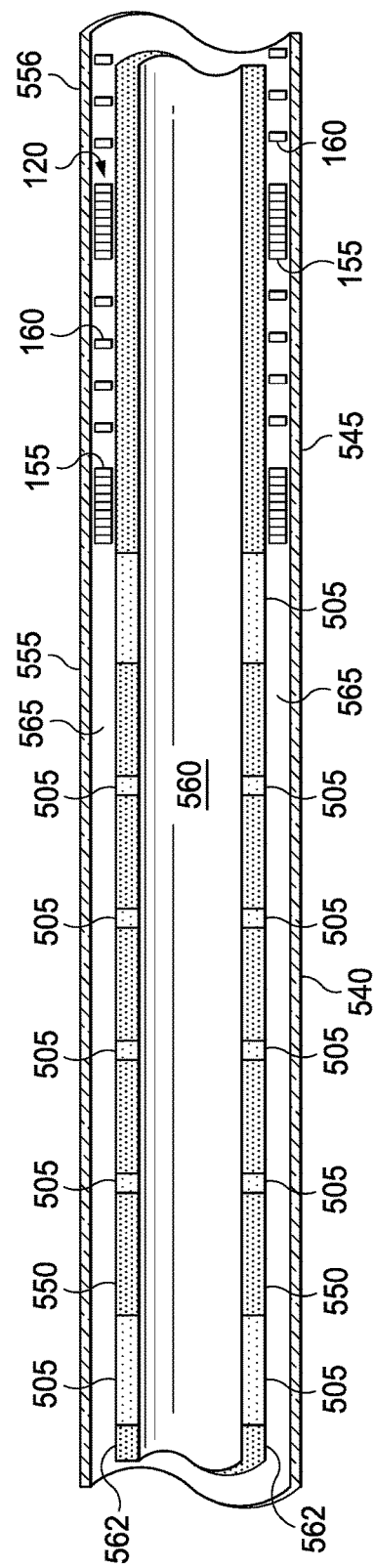

FIG. 10 is an illustration of a cross-sectional view of a distal portion of the exemplary catheter shown in FIG. 9, including exemplary inked markers and a portion of an exemplary marker coil.

Figure 11:
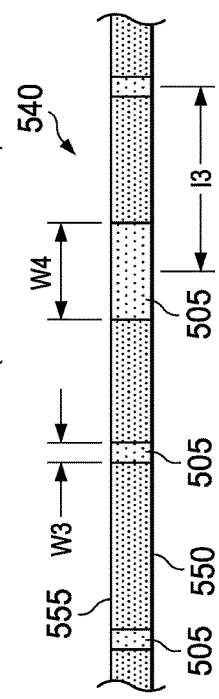

FIG. 11 is a diagrammatic illustration of a proximal portion of the exemplary imaging catheter shown in FIG. 9, including exemplary inked markers.

Figure 12:
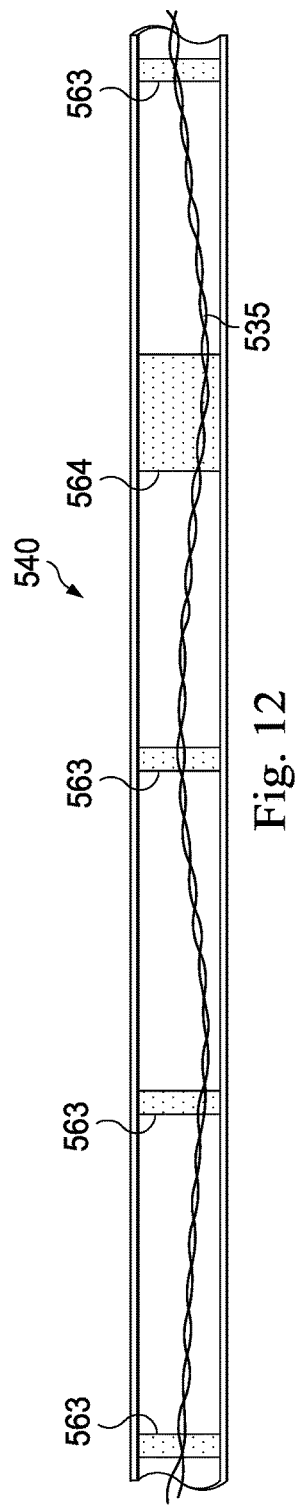

FIG. 12 is a schematic illustration of exemplary inked markers within an exemplary catheter according to one embodiment of the present disclosure.

Figure 13:
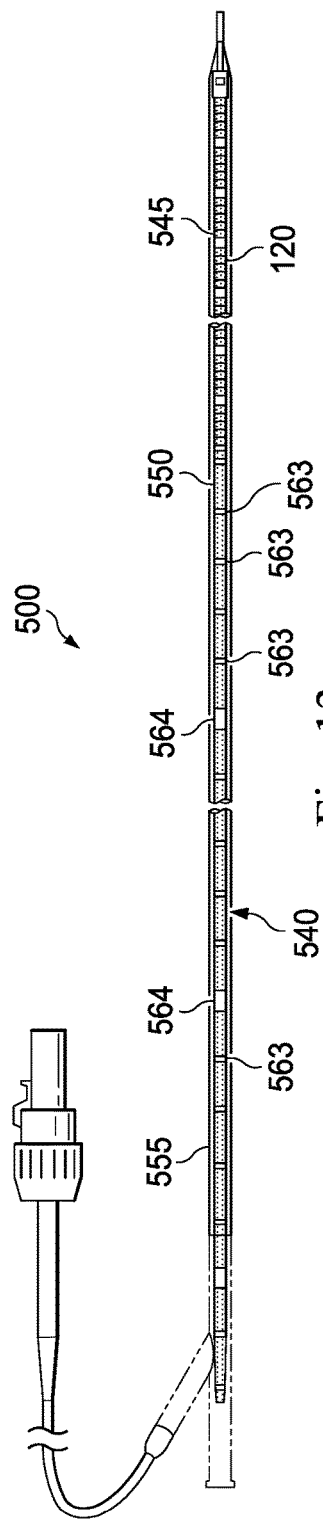

FIG. 13 is a diagrammatic illustration of the exemplary imaging catheter shown in FIG. 9, including exemplary inked markers and a portion of an exemplary marker coil.

Figure 14:
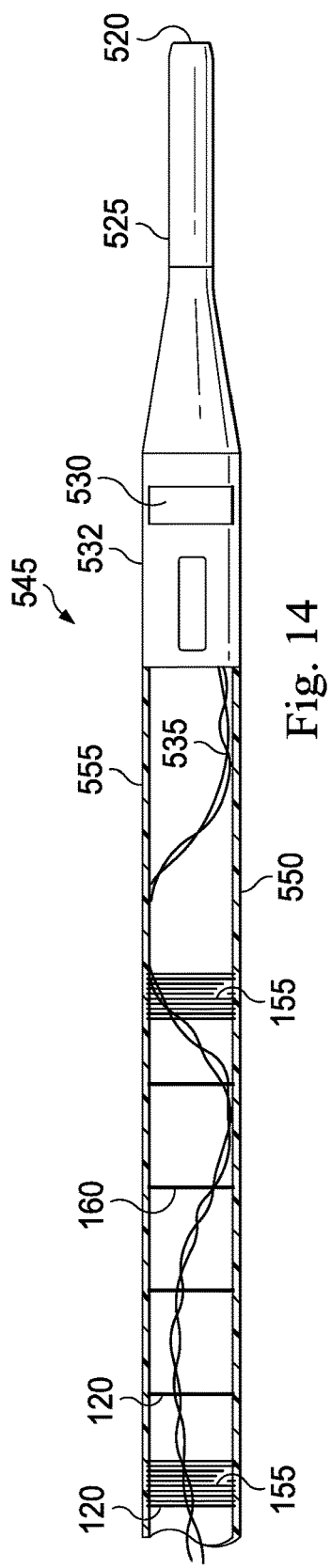

FIG. 14 is a schematic illustration of a distal portion of the exemplary imaging catheter shown in FIG. 9, including a portion of an exemplary marker coil, an imaging device, and a distal tip.

Figure 15:
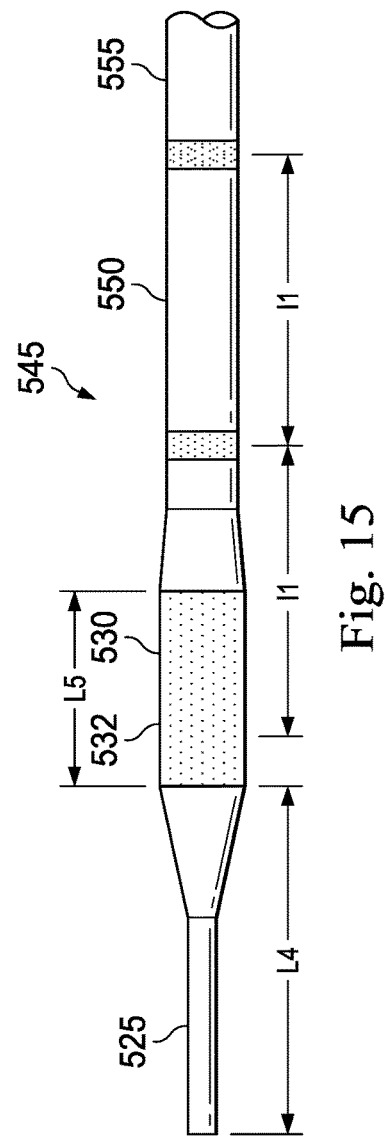

FIG. 15 is a diagrammatic illustration of a distal portion of the exemplary imaging catheter shown in FIG. 9, including exemplary inked markers.

FIG. 16 is an illustration of the exemplary imaging catheter shown in FIG. 9 positioned within a vessel with the imaging device positioned at a first end of an aneurysm.

FIG. 17 is an illustration of the exemplary imaging catheter shown in FIG. 9 positioned within a vessel with the imaging device advanced to a second end of an aneurysm.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure describes devices, systems, and methods to assist health care providers with accurate anatomical structure and/or lesion characterization using external and/or internal imaging. The accurate measurement of anatomical structures and lesions may assist the health care provider in diagnosing a condition, deciding on the appropriate course of treatment, treating the condition, and evaluating the results of the treatment. In one aspect, the present disclosure describes devices, systems, and methods for providing flexible radiopaque markers associated with tubular medical devices such as catheters. In particular, the present disclosure describes a catheter including a radiopaque marker coil having alternating coiled regions of varying pitch and, thus, regions of more and less radiopacity. The marker coil disclosed herein provides an apparatus that can be integrated with tubular medical devices and achieve the radiodensity necessary to be able to visualize and characterize anatomical regions of interest without compromising the flexibility and maneuverability of the device. The marker coil comprises a single length of material that is coiled into tightly wound sections having a closed pitch and loosely wound sections having an open pitch. The tightly wound sections form areas of greater radiopacity while the loosely wound sections form areas of less radiopacity. As the catheter curves to travel through a patient's bodily passages, the marker coil can flex to accommodate for the curvature of the catheter without limiting the flexibility of the catheter. In one aspect, the marker coil is positioned within the catheter wall at a distal portion of the catheter. Moreover, the marker coil disclosed herein may be manufactured more efficiently and at less cost than other radiopaque markers. In another aspect, the present disclosure describes a catheter including the radiopaque marker coil on a distal portion of the catheter as well as proportionally spaced inked marker bands on a proximal portion of the catheter. The combination of radiopaque and inked markers facilitate the ability of the user to accurately estimate internal anatomical structure and lesion measurements.

It should be appreciated that while the exemplary embodiment is described in terms of a catheter, the present disclosure is not so limited. Thus, for example, using the marker coil and/or the inked markers disclosed herein on a tubular medical device such as, by way of non-limiting example, a guidewire or a probe, is within the spirit and scope of the present disclosure.

Referring to FIG. 1, shown therein is a catheter 100 comprising an elongated, flexible tubular member or body 102 including a central lumen 105 that allows the passage of contents from a proximal end 110 through a distal end 115 of the catheter 100. A radiopaque marker coil 120 is positioned at a distal portion 125 of the body 102. In general, the catheter 100 is sized and shaped for use within an internal structure of a patient, including but not limited to a patient's arteries, veins, heart chambers, neurovascular structures, gastrointestinal system, pulmonary system, and/or other areas where internal access of patient anatomy is desirable. In that regard, depending on the particular medical application, the catheter 100 is configured for use in cardiology procedures, neurovascular procedures, pulmonary procedures, endoscopy procedures, colonoscopy procedures, natural orifice procedures (such as Natural Orifice Transluminal Endoscopic Surgery (NOTES)), and/or other medical procedures.

The body 102 is shaped and sized for insertion into bodily passages of a human patient. In the pictured embodiment, the body 102 is shaped and configured for insertion into a lumen of a blood vessel (not shown) such that a longitudinal axis LA of the catheter 100 aligns with a longitudinal axis of the vessel at any given position within the vessel lumen. In that regard, the straight configuration illustrated in FIG. 1 is for exemplary purposes only and in no way limits the manner in which the catheter 100 may curve in other instances. Generally, the elongate body 102 may be configured to take on any desired arcuate profile when in the curved configuration. In one instance, the body 102 has an overall length from the proximal end 110 to the distal end 115 of at least 90 cm and in some embodiments extending to 150 cm. Other lengths are also contemplated. In some instances, the body 102 has an external diameter ranging from 2 F to 9 F (i.e., 0.67 mm to 3 mm).

The body 102 is formed of a flexible material such as, by way of non-limiting example, high density polyethylene, polytetrafluoroethylene, Nylon, block copolymers of polyamide and polyether (e.g., PEBAX), polyolefin, polyetherester copolymer, polyurethane, polyvinyl chloride, combinations thereof, or any other suitable material for the manufacture of flexible, elongate catheters. In the pictured embodiment, the body 102 is connected at the proximal end 110 to an adapter 130, which is configured to couple the catheter 100 to another medical device at a proximal port 135 and/or through an electrical connection 137. Various medical devices that may be coupled to the catheter 100 at the proximal port 135 include, by way of non-limiting example, a storage vessel, a disposal vessel, a vacuum system, a syringe, an infusion pump, and/or an insufflation device. Various devices that may be coupled to the catheter 100 by the electrical connection 137 include, by way of non-limiting example, an energy generator (e.g., an ultrasound generator), a power source, a patient interface module ("PIM"), a computer system, and/or a surgical console.

The lumen 105 is shaped and configured to allow the passage of fluid, cellular material, or another medical device (e.g., a guidewire) from the proximal end 110 to the distal end 115. In some embodiments, the lumen 105 is sized to accommodate the passage of a guidewire. In such an embodiment, the lumen 105 has an internal diameter greater than 0.014 inches.

The distal end 115 is configured to be inserted into a body cavity, tissue, or tubular organ system of a patient. In some embodiments, the catheter 100 includes a distal tip 140 terminating in the distal end 115. In some embodiments, the distal tip 140 is tapered to facilitate insertion of the body 102 into a patient. In other embodiments, the distal tip 140 may be blunt, angled, or rounded.

The marker coil 120 is coiled or wound about the distal portion 125 of the body 102, and has a length L extending from a first end 145 to a second end 150. In various embodiments, the marker coil 120 may have a length L ranging from 1 cm to 150 cm. In the pictured embodiment, for example, the marker coil 120 has a length L of 24 cm. The marker coil 120 comprises a single length of material that is coiled into tightly wound sections 155 having a closed pitch and loosely wound sections 160 having an open pitch and greater inter-coil spacing than the tightly wound sections. In the pictured embodiment, the marker coil 120 includes 25 tightly wound sections 155. In other embodiments, the marker coil may have any number of tightly wound sections. The tightly wound sections 155 form areas of greater radiopacity while the loosely wound sections 160 form areas of less radiopacity. Thus, the tightly wound sections 155 effectively form radiopaque markers separated from each other by the loosely wound sections 160. In one embodiment, the radiopaque material has an external diameter ranging from 0.022 in. to 0.080 inches (i.e., 0.56 mm to 2.03 mm). In some embodiments, the radiopaque material has an external diameter approximating the external diameter of the catheter body.

As shown in FIG. 2, illustrating a section of the distal portion 125 of the body 102, the marker coil 120 comprises the tightly wound sections 155 separated by the loosely wound sections 160. As mentioned above, the marker coil 120 is formed of a single length of radiopaque material that has been wound into areas of varying pitch. The radiopaque material may be one or more radiopaque metals including, but not limited to, gold, tungsten, iridium, rhodium, platinum, barium, bismuth, and combinations and/or alloys thereof. However, any material with a high enough radiodensity when shaped into a tightly wound section 155 is suitable for the marker coil 120. For example, the marker coil 120 may be formed of lower cost alternatives to precious metals with equivalent radiodensity. In some embodiments, the radiopaque material is a radiopaque polymer, which may comprise a matrix of a polymeric material in combination with a radiopaque metal, such as are described above.

As shown in FIGS. 2 and 3, the tightly wound sections 155 are tightly wound areas of the marker coil 120 that form blocks of greater radiopacity or radiodensity than the loosely wound sections 160. In some embodiments, the tightly wound sections 155 have a width W ranging from 1.0 mm to 2.0 mm. In the pictured embodiment in FIG. 3, the tightly wound sections 155 have a width W of approximately 1.5 mm. Both the tightly wound sections 155 and the loosely wound sections 160 retain the ability to flex, albeit to different degrees. Given the increased flexibility of the radiopaque tightly wound sections 155, the tightly wound sections 155 may have greater widths W (and greater resultant visibility) than rigid, metallic marker bands. Thus, the tightly wound sections 155 form flexible radiopaque markers with spring-like functionality that are capable of curving with the catheter 100 as it traverses through tortuous anatomy without causing the inadvertent catheter kinking and/or trauma that can be caused by rigid marker bands.

The tightly wound sections 155 have a closed pitch while the loosely wound sections have an open pitch. In other words, as shown in FIG. 3, the tightly wound sections 155 are formed of tightly compressed individual coils 162 of the marker coil 120 having little to no space between them, while the loosely wound sections 160 are formed by coils 162 having greater space between centers of adjacent coils 162. In some embodiments, the pitch of the coils 162 in the loosely wound sections 160 may range from 1.1938 mm (0.047 inches) to 1.3462 mm (0.053 inches). In the pictured embodiment, the loosely wound sections 160 are formed by four loosely wound turns or coils 162 of the marker coil 120. However, the loosely wound sections 160 may be formed by any number of coils 162.

In one embodiment, the marker coil 120 is manufactured by stretching a tightly compressed coil at constant intervals past the recovery point of the coil material, thereby creating alternating areas of tightly wound coil and loosely wound coil. Stretching the coil past its recovery point "sets" the intervals between the individual coils (e.g., coils 162) and creates constant intervals between the tightly wound sections 155 and the loosely wound sections 160. For example, in the pictured embodiment in FIG. 3, the tightly wound sections 155 are separated from one another by a constant interval I1, which reflects a fixed distance between adjacent tightly wound sections 155. Similarly, the loosely wound sections 160 are separated from one another by a constant interval I2, which reflects a fixed distance between adjacent loosely wound sections 160. The interval I1 may vary in different embodiments depending upon the particular application desired. For example, in various embodiments, the interval I1 may range from 0.5 cm to 5 cm. In some embodiments, the interval I1 of the marker coil is 1 cm. Stretching the coil past its recovery point to create constant intervals between the tightly wound sections 155 and the loosely wound sections 160, as well as between the individual coils 162, strengthens the marker coil 120.

Figure 5A:
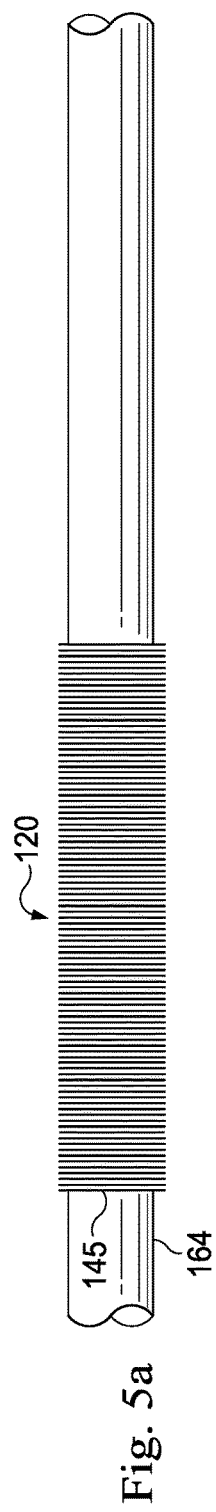
Figure 5B:
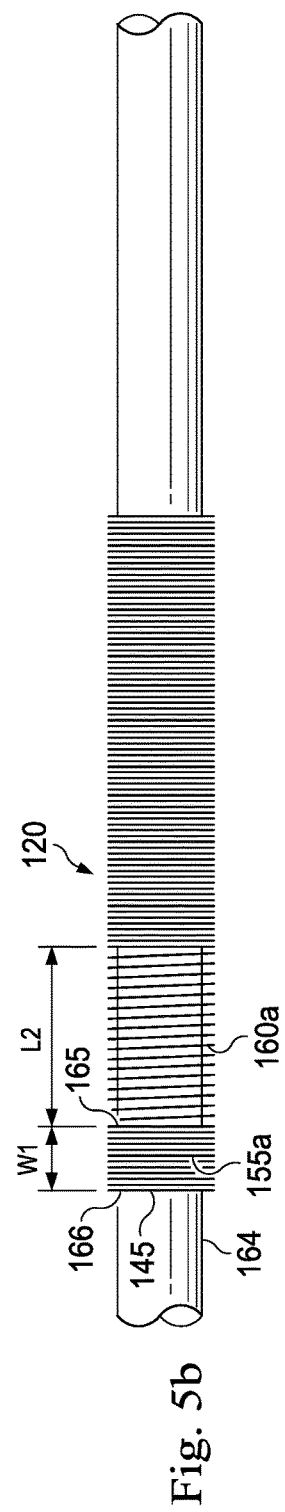
Figure 5C:
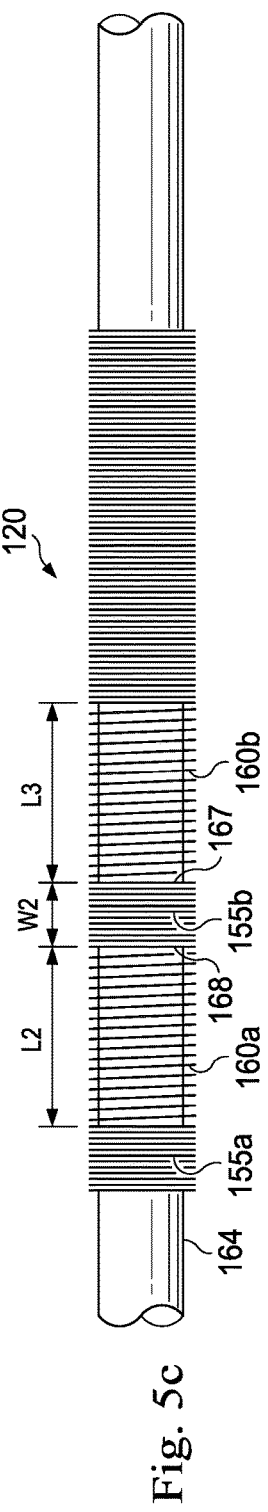
Figure 5D:
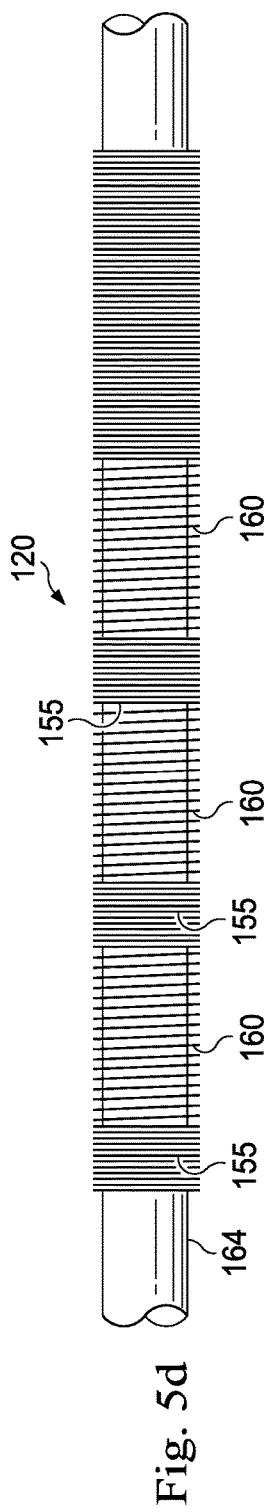

As shown in FIG. 4, in one embodiment, the marker coil 120 may be manufactured on a mandrel 164. As shown in FIG. 5a, the marker coil 120 may be fixed (e.g., with a fixation device) in an un-stretched condition at the first end 145 about the cylindrical mandrel 164 before being stretched at constant intervals past the recovery point of the coil material, thereby creating alternating areas of tightly wound sections 155 and loosely wound sections 160. In particular, as shown in FIG. 5b, a tightly wound section 155a of the marker coil 120 may be releasably anchored to the mandrel 164 at a coil 165 before the marker coil is stretched in a direction opposite the first end 145 to create a loosely wound section 160a of a desired length L2. The distance between a coil 166 and the coil 165 may be selected based upon a desired width W1 of the tightly coiled section 155a. As shown in FIG. 5c, the marker coil 120 may be releasably anchored to the mandrel 164 at a coil 167 of a tightly wound section 155b before the marker coil is stretched in a direction opposite the first end 145 to create a loosely wound section 160b of a desired length L3. The distance between a coil 168 and the coil 167 may be selected based upon a desired width W2 of the tightly wound section 155a. In some embodiments, the widths W1, W2 may be substantially the same, but in other embodiments, the widths of individual tightly wound sections may vary in accordance with the desired application for the radiopaque markers. Similarly, in some embodiments, the lengths L2, L3 may be substantially the same, but in other embodiments, the lengths of individual loosely wound sections may vary in accordance with the desired application. As illustrated by FIG. 5d, this process may be repeated until the marker coil 120 comprises the desired number and arrangement of alternating tightly wound sections 155 and loosely wound sections 160. Thus, the marker coil 120 has highly radiopaque tightly wound sections 155 alternating with less radiopaque loosely wound sections 160 at substantially constant intervals, allowing the catheter 100 to serve as an internal marking or measuring device.

In the embodiment shown in FIG. 6, the marker coil 120 is at least partially enclosed within an outer wall 170 of the catheter body 102. The outer wall 170 extends from an inner surface 172 to an outer surface 174. In the pictured embodiment, the inner surface 172 forms a luminal surface of the catheter 100 adjacent the lumen 105. In at least one embodiment, the marker coil 120 is completely enclosed between the inner surface 172 and the outer surface 174. In some embodiments, an edge or end of the marker coil may by exposed through the outer surface 174 and/or the inner surface 172 of the outer wall 170. For example, in some embodiments it may be desirable for an edge or end of the marker coil 120 to protrude from the wall 170 to anchor itself or other catheter components (e.g., a balloon or a stent) to the body 102.

The marker coil 120 can be placed within and/or about the outer wall 170 in accordance with a variety of methods. In the pictured embodiment, the outer wall 170 includes a lumen 176 sized and configured to receive the marker coil 120 during manufacture of the catheter 100 without increasing the outer diameter D or profile of the body 102 of the catheter 100. The lumen 176 comprises an annular space extending between the inner surface 172 and the outer surface 174. The space within the lumen 176 allows the radiopaque marker coil 120 to bend and flex freely beneath the outer wall 170. In some embodiments, the marker coil 120 may be wound directly onto the catheter (i.e., into the inner surface 172) under tension before the incorporation of the outer surface 174 to form a series of flexible radiopaque markers that are embedded within the outer wall 170. For example, the outer surface 174 of the outer wall 170 may be applied as a polymeric solution over the marker coil 120, or as a heat-shrink film that is wrapped around the coil 120.

In some instances, such as where the radiopaque material of the marker coil 120 is a metal wire, the material of the outer wall 170 is softer than the radiopaque material of the marker coil. In such instances, the marker coil 120 may be directly embedded into the outer wall 170 by sliding the marker coil over the distal portion 125 of the body 102 and directly apply force to the marker coil to push it into the material of the outer wall. For example, in some embodiments, a compressive apparatus (e.g., a roller assembly) may be used to physically press the marker coil 120 circumferentially and along its length into the outer wall 170 of the catheter 100. In some instances, the outer surface 174 may include indentations, grooves, or other surface features shaped and configured to receive the marker coil 120 without disrupting the inner surface 172 or increasing the outer diameter D or profile of the body 102 of the catheter 100. In some embodiments, the marker coil 120 is incorporated into the outer wall 170 of the catheter 100 in such a manner as to maintain a smooth outer surface of the catheter 100. Such a smooth surface has improved lubricity over a comparable catheter having metallic marker bands disposed around the outer wall 170.

FIG. 7 is a schematic illustration of the marker coil 120 enclosed within an outer wall 170 of the body 102 of the catheter 100. In some embodiments, the marker coil 120 acts as a support mechanism to the wall 170 of the catheter 100 and lends an additional degree of stiffness to the distal portion 125 of the body 102 of the catheter 100. As a result, the distal portion 125 may be provided with greater longitudinal stiffness, which may improve the device pushability of the catheter 100.

The method of stretching a single coil to form the more radiopaque, tightly wound sections 155 separated by constant intervals I1 creates a bound series of radiopaque markers, and the method of integrating the unitary marker coil 120 with the catheter 100 avoids the need to individually place radiopaque markers along a medical device. The embodiments disclosed herein eliminate the need to individually place or swage separate radiopaque markers onto a medical device. Instead, the unitary marker coil 120 comprises several constantly spaced tightly wound sections 155 or radiopaque markers that may be integrated into the body 102 of the catheter 100 without disturbing their predetermined distances from one another. Therefore, the embodiments disclosed herein avoid the positioning errors associated with the discrete placement of individual radiopaque markers (e.g., marker bands). Moreover, the embodiments disclosed herein allow for a less expensive and possibly less time-consuming manufacturing process than that required by the discrete placement of individual radiopaque markers.

FIG. 8 illustrates a fluoroscopic or X-ray image 400 showing the catheter 100 positioned within a patient. In particular, the distal portion 125 of the catheter 100 is shown extending through the coronary vasculature. The tightly wound sections 155 of the marker coil 120 are prominently visible on the image 400, while the less radiopaque loosely wound sections 160 are less prominently highlighted on the image 400. A healthcare provider may utilize the marker coil 120 to evaluate, localize, and measure anatomical structures and lesions as described below in relation to FIGS. 16 and 17. In addition, the healthcare provider may draw conclusions about the three-dimensional structure or plane of curvature of the intraluminal structure and/or lesion by observing the relative distances between adjacent tightly wound sections 155. For example, shortened or absent intervals I1 between adjacent tightly wound sections 155 on the image 400 may indicate an out-of-plane deflection of the catheter 100. In other words, shortened or absent intervals I1 between adjacent tightly wound sections 155 on the image 400 may indicate curvature of the catheter 100 in a third dimension or a z-plane. Such data could be used in combination with angiography and/or intravascular imaging to generate a three-dimensional representation of the marker coil 120 and/or the intraluminal structure and/or lesion where the marker coil is located.

Referring back to FIG. 1, in some embodiments, the catheter 100 includes an imaging device, such as, by way of non-limiting example, an intravascular ultrasound ("IVUS") transducer 200. Thus, in some embodiments, the catheter 100 may comprise an IVUS catheter. In such embodiments, the catheter 100 may be connected at the electrical connection 137 to an IVUS imaging system. In the pictured embodiment, the distal tip 140 houses the transducer 200. The marker coil 120 provides radiopaque markers in the form of the tightly wound sections 155 to assist in positioning the transducer 200 within a patient's vasculature and obtaining accurate visualization and measurements of the patient's vessels. In some instances, the imaging device may be used to determine the morphology and pathology of a target lesion within a patient's anatomy (e.g., a restriction within a vessel). The radiopaque tightly wound sections 155 allow for the accurate localization and measurement of such a lesion. Intraluminal imaging may be done as an initial step to help determine the best applicable therapy, to observe a therapeutic measure in real-time, or as a later step to assess the results of a given therapy.

It should be appreciated that while the exemplary embodiment is described in terms of an ultrasonic device to render images of a vascular object, the present disclosure is not so limited. It should be noted that the catheter 100 depicted herein is not limited to a particular type of device, and includes any of a variety of imaging devices. Thus, for example, using backscattered data (or a transformation thereof) based on other sources of energy, such as electromagnetic radiation (e.g., light waves in non-visible ranges such as used in Optical Coherence Tomography, X-Ray CT, spectroscopy, etc.), to render images of any tissue type or composition (not limited to vasculature, but including other structures within a human or non-human patient) is within the spirit and scope of the present disclosure.

With reference to FIG. 1, in some embodiments, the catheter 100 includes an expandable device 300, such as, by way of non-limiting example, a balloon apparatus and/or a stent. The expandable device 300 may be positioned about the distal tip 140 and/or the distal portion 125. The expandable device 300 may be positioned around the coil marker 120 such that the radiopaque portions of the coil marker 120 can be visualized on fluoroscopy through the expandable device as the catheter 100 is maneuvered through the patient's body. The marker coil 120 provides radiopaque markers in the form of the tightly wound sections 155 to assist in positioning the expandable device 300 within a patient's vasculature and obtaining accurate visualization and measurements of the patient's vessels. In some embodiments, the length of the expandable device 300 is at least as long as the length L of the coil marker 120 extending from the first end 145 to the second end 150.

In some instances, the catheter 100 is used to deliver a medical device such as a balloon, a stent, a graft, a stent-graft, a vena-cava filter, or other implantable medical device, hereinafter collectively referred to as the expandable device 300. For example, the expandable device 300 may comprise a self-expanding stent or may comprise a balloon used to deliver and/or deploy a balloon-expandable stent. In some instances, the expandable device 300 comprises a drug-eluting device such as a drug-eluting balloon or a drug-eluting stent. The radiopaque markers provided by the tightly wound sections 155 may assist in the precise intravascular delivery and deployment of the expandable device 300. In particular, the expansion of the expandable device 300 may be monitored using fluoroscopy-mediated visualization of the radiopaque tightly wound sections 155. In some instances, the expandable device 300 is positioned about the wall 170 of the catheter 100 in such a manner as to ensure that the expandable device 300 does not extend substantially beyond the length L of the marker coil 120.

Due to the non-linear nature of many body lumens, it is often desirable to measure the length of a body lumen along a center line extending axially through the center of the body lumen. Such measurements can be useful in selecting an appropriately sized luminal implant or prosthesis. In that regard, in some instances, the expandable device 300 comprises a positioning element shaped and configured to center the catheter 100 within a lumen (e.g., a curved lumen) so as to facilitate the accurate measurement of an intraluminal structure or lesion. Such an expandable device may have a diameter in an expanded state that at least corresponds to the diameter of the body lumen. In this way, the expandable device 300 can be expanded to center the catheter 100 within the body lumen, thereby allowing the length of the lesion (or area of interest within the lumen) to be measured along the center of the body lumen.

FIG. 9 shows an imaging catheter 500 including the marker coil 120 and a plurality of inked markers 505 according to one embodiment of the present disclosure. The imaging catheter 500 is substantially similar to the catheter 100 except for the differences noted herein. The catheter 500 comprises an elongate, tubular member or body 510 extending from a proximal end 515 to a distal tip 525 that terminates at a distal end 520, an imaging device 530 disposed on an imaging housing 532, and an adapter 130 coupling the body 510 to a PIM 535.

The body 510 is substantially similar to the body 102 of the catheter 100 except for the differences noted herein. The body 510 includes a proximal shaft portion 540, which includes the plurality of inked markers 505, and a distal shaft portion 545, which includes the marker coil 120. As shown in FIG. 10, the body 510 comprises an inner tubular member 550 disposed co-axially within an outer tubular member 555. The inner tubular member 550 extends the length of the body 510 and is coupled at either end to the adaptor 130 and the distal tip 525 (shown in FIG. 9). In some embodiments, the inner tubular member 550 is heat bonded to the adapter 130 and the distal tip 525. However, any of a variety of coupling methods may be employed to secure the inner tubular member 550 to the adaptor 130 and the distal tip 525.

In the pictured embodiment, the inner tubular member 550 comprises a darkly colored, elongate, cylindrical tube. The inner tubular member 550 defines a lumen 560 extending the length of the body 510 from the adaptor 130 to the distal tip 525. The lumen 560 is substantially identical to the lumen 105 described above in relation to FIG. 1.

The outer tubular member 555 comprises a transparent cylindrical sleeve that extends from the adapter 130 to the imaging device housing 532. In some embodiments, the outer tubular member 555 is clear. In some embodiments, the outer tubular member 555 is secured to the adapter 130 and the imaging device housing 532 by means of an adhesive. However, any of a variety of coupling methods may be employed to secure the outer tubular member 555 to the adaptor 130 and the imaging device housing 532. The outer tubular member 555 includes a smooth outer surface 556 configured to reduce the amount of friction created on an introducer device during insertion and removal of the catheter 500, thereby facilitating smooth and accurate pullbacks during imaging procedures.

As shown in FIG. 10, the plurality of inked markers 505 are disposed on the inner tubular member 550. The inked markers 505 comprise direct visualization markers that may be viewed during use with the naked eye (or with the use of an endoscope), in contrast to the tightly wound sections 155 of the marker coil 120, which comprise radiopaque markers. The inked markers 505 comprise lightly-colored markings on an exterior surface 562 of the inner tubular member 550. The lightly-colored inked markers 505 appear clearly against a background of the darkly-colored inner tubular member 550 and can be visualized easily through the clear outer tubular member 555 with and without the use of light. In alternate embodiments, the inner tubular member may be light-colored while the inked markers are darkly-colored, provided there is adequate contrast between the colors of the inner tubular member and the inked markers to permit visualization through the outer tubular member 555. For example, in some embodiments, the inner tubular member 550 may have a dark color, such as black, dark blue, dark grey, or the like, while the inked markers 505 have a light color such as white, light blue, light green, pink, or the like. The high contrast between the plurality of inked markers 505 and the inner tubular member 550 facilitates visualization of the markers in a low light environment, such as a darkened operating room.

The inked markers 505 may be formed of a variety of suitable inks, which are typically indelible. Because the inked markers 505 are shielded from the patient's anatomy by the outer tubular member 555, the ink does not necessarily have to be biocompatible. In some embodiments, the inked markers 505 may be formed of a fluorescent substance, thereby enabling the inked markers to be more clearly visualized in a low light environment, such as a darkened operating room. The inked markers 505 can be applied to the inner tubular member 550 by any of a variety of suitable methods, including, without limitation, painting, spraying, masked dipping (i.e., dipping the body 510 in ink with parts of the body masked to avoid being coated by the ink), and electrostatic attraction.

FIG. 11 illustrates a portion of the proximal shaft portion 540, which includes the plurality of inked markers 505. In the pictured embodiment, the plurality of inked markers 505 comprise markers of different widths. In particular, the plurality of inked markers 505 comprise inked markers 563, which have a width W3, and inked markers 564, which have a width W4. In various embodiments, the widths of the individual inked markers may be uniform or different, depending upon the desired application of the inked markers 505 and/or the catheter 500. The widths of the individual inked markers may range from 0.5 mm to 5.5 mm. In at least one embodiment, the width W3 is approximately 1.0 mm and the width W4 is approximately 5.0 mm.

FIG. 12 illustrates the proximal shaft portion 540 of the catheter 500, including the inked markers 563, 564. In other embodiments, any number of inked markers 563 and the inked markers 564 may be positioned on the inner tubular member 550 in any of a variety of combinations or arrangements. In some embodiments, the inked markers 563 and 564 may have the same width, comprising a plurality of equally-sized inked markers. In some embodiments, the inked markers 563 may have a different color than the inked markers 564 to facilitate distinguishing the markers 563, 564 from one another during use. In the pictured embodiment in FIG. 13, the inked markers 563 and the inked markers 564 are arranged in a repeating pattern of four inked markers 563 and one inked marker 564. The inked markers 563 and the inked markers 564 are separated from one another by an interval I3. The interval I3 may vary in different embodiments depending upon the particular application desired. The interval I3 may range from 3.0 mm to 20.0 mm. For example, in the pictured embodiment in FIG. 11, the interval I3 measures approximately 1 cm, which reflects a fixed distance between adjacent inked markers 505.

Returning to FIG. 10, the outer tubular member 555 circumferentially and longitudinally surrounds the inner tubular member 550, creating an annular space or lumen 565 therebetween. In the pictured embodiment, the marker coil 120 is at least partially enclosed in the lumen 565 between the inner tubular member 550 and the outer tubular member 555 at the distal shaft portion 545. In at least one embodiment, the marker coil 120, including the tightly wound sections 155 and the loosely wound sections 160, is completely enclosed in the lumen 565 at the distal shaft portion 565. In the pictured embodiment of FIG. 9, the marker coil 120 comprises twenty-five tightly wound sections 155 separated from each other by approximately 1 cm.

FIGS. 14 and 15 show the distal shaft portion 545 of the catheter 500, including the imaging device 530 positioned proximal to the distal tip 525 at the imaging device housing 532. Electrical wires 535 extend longitudinally along a length of the catheter from the imaging device housing 532. The distal tip 525 is configured to be inserted into a body cavity, tissue, or tubular organ system of a patient. In the illustrated embodiment, the distal tip 525 is tapered to facilitate insertion of the body 510 into a patient. As shown in FIG. 15, the distal tip 525 has a length L4 ranging from 10 mm to 20 mm. In various embodiments, the length L4 varies depending upon the particular application of the catheter 500. For example, in the pictured embodiment, the length L4 is approximately 12 mm.

The image device housing 532 has a length L5 ranging from 1.5 mm to 10.0 mm. In various embodiments, a length L5 varies depending upon the particular type of imaging device 530 and the particular application of the catheter 500. In the pictured embodiment, the imaging device 530 comprises an ultrasound transducer (e.g., by way of non-limiting example, a solid state phased array, a rotational, FLIVUS, and/or PMUT transducer). However, in other embodiments, the imaging device 530 may comprise any of a variety of imaging devices, including, by way of non-limiting example, an OCT or laser-emitting device. For example, in the pictured embodiment where the imaging device 530 comprises an ultrasound transducer, the length L5 is approximately 6.5 mm.

In the pictured embodiment in FIG. 15, the tightly wound sections 155 of the marker coil 120 are separated from each other and the imaging device 530 by an interval I1, as described above in relation to FIG. 3. The interval I1 may vary in different embodiments depending upon the particular application desired. For example, in the pictured embodiment, the interval I1 of the marker coil 120 is 1 cm.

FIGS. 16 and 17 illustrate an exemplary instance where the catheter 500, with its combination of proximally-positioned inked markers 505 and its distally-positioned marker coil 120, can be used to assist the healthcare professional with accurate and efficient lesion measurement and evaluation. In FIG. 16, the distal shaft portion 545 of the catheter 500 is positioned within a vessel 600, which includes a intravascular lesion 605. In the pictured embodiment, the vessel 600 comprises an aorta and the intravascular lesion comprises an aortic aneurysm, which is an abnormal dilation of the aorta. However, the catheter 500 (or the catheter 100 described above) may be used to evaluate a variety of lesions and/or structures, as described further below.

In FIG. 16, the distal shaft portion 545 of the catheter 500 is shown positioned within the vessel 600 such that the marker coil 120 is located adjacent to the lesion 605. In particular, the distal-most tightly wound section 155c is positioned immediately proximal the lesion 605, which may be visualized with contrast during fluoroscopy, without contrast during fluoroscopy (i.e., by visualizing the radiopaque tightly wound sections 155), and/or with the use of the imaging device 530. During fluoroscopy, the tightly wound sections 155 of the marker coil 120 remain visible, thereby allowing the healthcare provider to position the marker coil 120 relative to margins of the lesion 605 to measure various dimensions of the lesion 605. In some instances, the healthcare professional may visualize the lesion 605 using fluoroscopy to accurately position the radiopaque tightly wound section 155c at a first end 606 of the lesion 605. In some instances, the healthcare professional may use the imaging device 530 to localize the lesion 605 and accurately position the radiopaque tightly wound section 155c at the first end 606 of the lesion 605. For example, the imaging device 530 may be used to localize relevant anatomical landmarks and/or the margins of the lesion 605. In some instances, the healthcare professional may use a combination of extravascular imaging (i.e., fluoroscopy) and intravascular imaging (i.e., with the imaging device 530) to localize the lesion 605 and accurately position the radiopaque tightly wound section 155c at the first end 606 of the lesion 605.

Intravascular imaging can occur before or after interventional treatment. When used before such treatments, the images may aid the healthcare profession in localizing the lesion 605 and in deciding whether and/or how to treat the lesion. For example, in the case of aneurysms, the imaging device 540 may be used to evaluate the health of the tissue wall prior to selecting an implanting a stent graft to repair the aneurysm and selecting anchor points for the stent/graft. Moreover, the imaging device 540 may be used to determine both the position and orientation of the tightly wound sections 515 (i.e., as the distal shaft portion 545 is curved to approximate the boundaries of the lesion 605) to assist in evaluating the lesion 605. For example, the imaging device 540 may be utilized to determine position of individual tightly wound sections 515 relative to each other to evaluate the shape and/or curvature of the lesion 605. The resulting data may be utilized to construct a three dimensionally significant representation of the lesion 605 as indicated by the positions of the tightly wound sections 515. Such a representation could yield a length, diameter, and/or radius of curvature of a lesion 605, all of which could be used to assist in the selection of an appropriately sized prosthetic or implant, such as a stent graft for repairing an aneurysm.

When used after a given treatment, the images may aid the healthcare professional in the assessment and documentation of the results of the treatment. Utilizing intravascular imaging from the imaging device 540 in combination with the radiopaque tightly wound sections 155 of the marker coil 120 enables the healthcare provider to use less contrast during the localization and the measurement of the lesion 605. Moreover, the positions of the radiopaque tightly wound sections 155 observed with fluoroscopy may be co-registered with the positions of the tightly wound sections 155 observed with intravascular imaging to enhance the evaluation, localization, and measurement of the lesion 605.

Once the distal-most tightly wound section 155c is positioned at the first end of the lesion 605, the healthcare provide can note the relevant inked markers 505 as described below and perform whatever diagnostic and/or therapeutic measures may be indicated for the particular procedure he or she is performing. Thereafter, the healthcare provider can advance the catheter 500 into the vessel 600 until the tightly wound section 155c is positioned at a second end 607 of the lesion 605.

In FIG. 17, the distal-most tightly wound section 155c is positioned at a second end 607 of the lesion 605, which may be visualized with contrast during fluoroscopy, without contrast during fluoroscopy (i.e., by visualizing the radiopaque tightly wound sections 155), and/or with the use of the imaging device 530 as described above. The healthcare provider can use the marker coil 120 to estimate the length and/or other dimensions of the lesion 605. In some instances, the healthcare provider can observe which particular tightly wound section 155d is positioned at the first end 606 of the lesion 605 when the distal-most tightly wound section 155c is positioned at the second end 607 of the lesion 605. By comparing the tightly wound section 155c to the tightly wound section 155d, the healthcare provider may estimate the length of the lesion 605. In particular, by counting the number of intervals I1 between the tightly wound section 155c and the tightly wound section 155d, and correlating that number of intervals to a length measurement, the healthcare provider can estimate the length of the lesion 605. As described above, the spacing between the tightly wound sections 155 can be of a constant length interval I1 so that the healthcare professional can convert the difference in the number of intervals into a corresponding length measurement. For example, in the example shown in FIGS. 16 and 17, there are nine intervals I1 between the tightly wound section 155c and the tightly wound section 155d. Given that each interval I1 of the marker coil 120 measures 10 mm or 1 cm, the length of the lesion 605 is approximately 900 mm or 9 cm. Thus, the multiple tightly wound sections 155 of the marker coil 120 provide several radiopaque markers that allow for more accurate measurement of various dimensions of an anatomical structure and/or lesion than a measuring device having only a few radiopaque markers.

The plurality of inked markers 505 allow the healthcare professional to visually detect how far the catheter 500 is axially moved with respect to a reference point such as a proximal end 610 of an introducer 615. At least some of the proximal shaft portion 540 of the catheter 500 is positioned outside the patient's body, allowing the healthcare professional to estimate the length of the catheter 500 that has been inserted into the patient's body by observing the number of inked markers 505 still visible outside the patient's body. In addition, the healthcare professional may estimate the length of the intravascular lesion 605 by noting a first number of externally visible inked markers 505 when the catheter 500 is positioned at the first end 606 of the lesion 605 as shown in FIG. 16, noting a second number of externally visible inked markers 505 when the catheter 500 is positioned at the second end 607 of the lesion 605 as shown in FIG. 17, and comparing the two values. In particular, the difference between the first number and the second number can be used to estimate the length of the lesion 605. As described above, the spacing between the inked markers 505 can be of a constant length interval so that the healthcare professional can convert the difference in the number of inked markers into a length measurement corresponding to how far the catheter 500 has axially moved with respect to a reference point such as a proximal end 610 of an introducer 615.

In another instance, the healthcare professional can observe a particular inked marker 505a present at a reference point outside the patient's body, such as the proximal end 610 of the introducer 615, when the catheter 500 is positioned at the first end 606 of the lesion 605 as shown in FIG. 16, observe a particular inked marker 505b present at the same reference point when the catheter 500 is positioned at the second end 607 of the lesion 605 as shown in FIG. 17, and comparing the length measurements indicated by the inked markers 505a, 505b. Each inked marker 505 is positioned a particular distance from the proximal end 515 of the catheter 500. For example, if the inked marker 505a is positioned 30 cm from the proximal end 515 and the inked marker 505b is positioned 22 cm from the proximal end 515, the healthcare professional may estimate that the length of the lesion 605 is 8 cm.

Once the lesion 605 has been measured, the healthcare provide can perform whatever diagnostic and/or therapeutic measures may be indicated for the particular procedure he or she is performing. For example, in some embodiments, the healthcare professional may advance the catheter 500 into the lesion 605 and image the lesion 605 using the imaging device 530. In other instances, the healthcare professional may expand an expandable device similar to the expandable device 300 shown in FIG. 1. Knowing the accurate length and/or other dimensions of the lesion 605 will help the healthcare provider to determine the appropriate course of treatment, appropriately evaluate the results of a given treatment, and/or appropriately position any implantable devices for treating the lesion 605. For example, in the situation illustrated by FIGS. 16 and 17, the healthcare provider may select an appropriately sized stent and expand the stent within the lesion 605 (i.e., an aneurysm) within the vessel 600.

Embodiments in accordance with the present disclosure provide users with an accurate and efficient device, system, and method for evaluating, localizing, and measuring anatomical structures and/or lesions to plan an appropriate treatment course and/or evaluate a given treatment. Proximal inked markers and/or a distal radiopaque marker coil in accordance with the present disclosure may be used alone or in combination in a variety of applications to evaluate, localize, and measure anatomical structures and/or lesions. For example, but not by way of limitation, embodiments of the present disclosure may be used to assist in evaluating an intraluminal site for implantation of a prosthesis (e.g., a drug-eluting balloon, a drug-eluting stent, a stent graft, a bioresorbable stent), PTCA balloon location, an endovascular aneurysm repair (e.g., of the abdominal or thoracic aorta), IVC filter placement (e.g., in the inferior vena cava), evaluation of tumor growth/response to treatment, and a variety of other procedures previously utilizing a separate measuring device (e.g., a ruler) for lesion measurement. In addition, embodiments of the present disclosure may be used to monitor the position and/or efficacy of already implanted devices such as, but not by way of limitation, stents, stent grafts, drug-eluting stents, drug-eluting balloons, and orthopedic implants (e.g., bone screws or hip, shoulder, or knee implants). Moreover, the markers of the present disclosure enable the elimination of at least one pigtail marker catheter exchange in several procedures, such as a low contrast endovascular aneurysm repair procedure, thereby accelerating the process of stent-graft length sizing assessment. Some embodiments of the present disclosure may be used in a variety of organ systems such as, but not by way of limitation, the circulatory system, the lymphatic system, the digestive system, the pulmonary system, the orthopedic system, and the neurological system.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A catheter comprising:
a flexible elongate member comprising a distal portion and a proximal portion, the flexible elongate member comprising an inner tubular member disposed coaxially within an outer tubular member, the inner tubular member defining a central lumen, the outer tubular member defining an annular lumen between the inner tubular member and the outer tubular member;
a single wire having a plurality of coils wound at a first pitch to form a plurality of radiopaque markers positioned at the distal portion of the flexible elongate member, wherein each of the coils wound at the first pitch is spaced apart from the other radiopaque markers by a portion of the single wire that is wound at a second pitch for a span of a first distance, wherein the second pitch is less than the first pitch; and
a plurality of visible markers disposed on the inner tubular member at the proximal portion,
wherein at least a portion of the outer tubular member is optically transparent such that a number of the visible markers disposed on the proximal portion of the inner tubular member are visible through the optically transparent portion of the outer tubular member.

2. The catheter of claim 1, wherein the plurality of visible markers comprise inked markers.

3. The catheter of claim 1, wherein the plurality of visible markers comprise fluorescent markers.

4. The catheter of claim 1, wherein each of the plurality of visible markers is spaced apart from the other visible markers by a second distance that is proportionally spaced with respect to the first distance between the radiopaque markers such that the visible markers indicate a length of a structure of a patient body as at least one of the plurality of radiopaque markers is advanced from a first position proximate a first end of the structure to a second position proximate an opposite end of the structure.

5. The catheter of claim 4, wherein the plurality of visible markers comprise a light color and the inner tubular member comprises a dark color.

6. The catheter of claim 5, wherein the light color comprises at least one of white, light blue, light green, or pink, and wherein the dark color comprises at least one of black, dark blue, or dark grey.

7. The catheter of claim 1, wherein the plurality of visible markers comprise a first subset of visible markers each comprising a first width and a second subset of the visible markers each comprising a second width different than the first width.

8. The catheter of claim 7 wherein the plurality of visible markers are arranged in a repeating pattern comprising one visible marker of the second subset and a plurality of visible markers of the first subset.

9. The catheter of claim 8, wherein two adjacent visible markers of the second subset are spaced from one another by the plurality of visible markers of the first subset such that consecutive visible markers of the second subset are spaced from one another by a second distance.

10. The catheter of claim 1, wherein the radiopaque markers are tightly wound sections of the single wire, and wherein the single wire provides an alternating series of the tightly wound sections of the first pitch having greater radiopacity and loosely wound sections of the second pitch that have less radiopacity than the tightly wound sections.

11. The catheter of claim 10, wherein the radiopaque markers are wound within the annular lumen between the inner tubular member and the outer tubular member at the distal portion of the elongate member.

12. The catheter of claim 10, wherein the tightly wound sections of the single wire are uniformly spaced from each other by loosely wound sections.

13. The catheter of claim 10, wherein the tightly wound sections are spaced apart by second distances defined by the loosely wound sections, and wherein the second distances are proportional to the first distances between the plurality of visible markers such that a length of a structure within the body of a patient is measureable based on a correlation between the first distances and the second distances.

14. The catheter of claim 1, further comprising an expandable device disposed on the distal portion of the elongate member.

15. The catheter of claim 1, further comprising an imaging device positioned at the distal portion of the flexible elongate member, wherein the imaging device is configured to provide an image of a region that comprises the radiopaque markers of the single wire to thereby permit measurement of an intravascular lesion by counting a number of the radiopaque markers that are proximate to the lesion in the image provided by the imaging device.

16. An intravascular device, comprising:
a flexible elongate member configured to be positioned within a vessel of a patient, the flexible elongate member comprising a distal portion and a proximal portion;
a single wire disposed at the distal portion of the flexible elongate member comprising a plurality of first sections wound at a first pitch to form a plurality of radiopaque markers wherein the radiopaque markers are each spaced apart from each other by a plurality of second sections each spanning a first distance between the first sections wherein the second sections of the single wire are each wound at a second pitch that is different from the first pitch; and
a plurality of ink markers disposed on the proximal portion of the flexible elongate member,
wherein adjacent ink markers of the plurality of ink markers are each spaced apart from each other by a second distance.

17. The device of claim 16, wherein the single wire forming the radiopaque markers separated by the first distance is wound within an annular lumen at the distal portion of the elongate member, and wherein the first sections of the single wire are each wound more tightly than the second sections of the single wire so that the first sections provide areas of greater radiopacity than the second sections of the single wire.

18. The device of claim 16 wherein the plurality of ink markers comprises a first subset of ink markers comprising a first width and a second subset of ink markers comprising a second width different from the first width, and wherein consecutive ink markers comprising the second width are interspersed by a plurality of ink markers comprising the first width.

19. The device of claim 16 wherein the ink markers are regularly spaced such that a change in a number of the ink markers visible as the at least one of the plurality of radiopaque markers is advanced from the first position to the second position corresponds to a length of a structure of a patient body.

20. The device of claim 16 further comprising an imaging device disposed at the distal portion of the flexible elongate member, wherein the imaging device is configured to provide an image of a region that comprises the radiopaque markers of the single wire to thereby permit measurement of an intravascular lesion by counting a number of the radiopaque markers that are proximate to the lesion in the image provided by the imaging device.

* * * * *